United States Patent [19]

Sorensen

[11] Patent Number: 4,625,550

[45] Date of Patent: Dec. 2, 1986

[54] METHOD AND APPARATUS FOR THE CONTINUOUS PSYCHROMETRIC MEASUREMENT OF THE CONCENTRATION OF A VAPOROUS COMPONENT IN A GAS

[76] Inventor: Ansgar C. H. Sorensen, Anemonevej 4, Allerod Dk-3450, Denmark

[21] Appl. No.: 732,697
[22] PCT Filed: Aug. 27, 1984
[86] PCT No.: PCT/DK84/00080
§ 371 Date: May 6, 1985
§ 102(e) Date: May 6, 1985
[87] PCT Pub. No.: WO85/01350
PCT Pub. Date: Mar. 28, 1985

[30] Foreign Application Priority Data

Sep. 13, 1983 [DK] Denmark .............................. 4151/83

[51] Int. Cl.⁴ ............................................ G01N 25/62
[52] U.S. Cl. .................................................... 73/338
[58] Field of Search ........................ 73/338, 338.3, 29

[56] References Cited

U.S. PATENT DOCUMENTS 3,157,049 11/1964 Stahlberg .............................. 73/338
3,645,134 2/1972 Kreiberg .............................. 73/338
4,518,566 5/1985 Sorensen .................................. 73/25

Primary Examiner—Stephen A. Kreitman
Attorney, Agent, or Firm—Watson, Cole, Grindle & Watson

[57] ABSTRACT

For the continuous psychometric measurement of the concentration of a vaporous component in a gas, i.e., the moisture content of air, by using a "dry" thermosensor and a "wet" thermosensor, the wet thermosensor is arranged in the open upper end of a vertical tube, to the lower end of which a liquid of the same kind as the vaporous component is supplied in such a manner that the liquid forms a small body of liquid on top of the tube, the body of liquid completely covering the wet thermosensor and overflowing from the top of the tube down along the upper surface of the tube in the form of a continuous liquid film.

3 Claims, 1 Drawing Figure

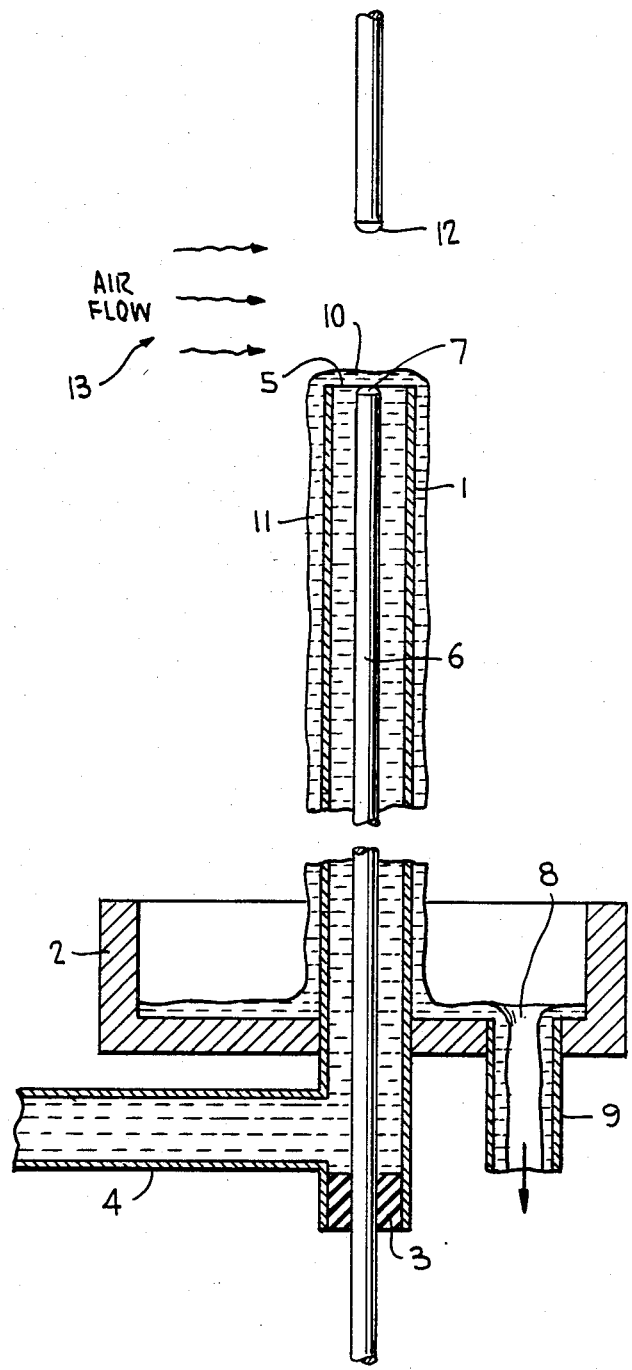

METHOD AND APPARATUS FOR THE CONTINUOUS PSYCHROMETRIC MEASUREMENT OF THE CONCENTRATION OF A VAPOROUS COMPONENT IN A GAS

BACKGROUND OF THE INVENTION

1. Field of the Invention

The invention relates to a method for the continuous psychrometric measurement of the concentration of a vaporous component in a gas, in particular the measurement of the moisture content of air.

1. The Prior Art

Psychrometric measurement of the concentration of a vaporous component in a gas takes place by causing the gas to flow past a "dry" thermosensor measuring the temperature of the gas flow, and a "wet" thermosensor, the surface of which is kept completely moistened with liquid of the same kind as the vaporous component. If the gas is unsaturated with the vaporous component, a vaporization of liquid will take place from the surface of the wet thermosensor, whereby, in the ideal case of a psychrometric measurement, the temperature of the wet thermosensor will drop until the supply of heat per time unit by convection from the flow of air is exactly equal to the energy consumption per time unit for the vaporization of liquid from the moistened surface. If the gas is saturated with the vaporous component, no vaporization takes place from the moistened surface, and the wet thermosensor assumes exactly the same temperature as the dry thermosensor.

Measurement of the temperature of the air by means of the dry thermosensor, measurement of the temperature of the wet thermosensor, and measurement of the pressure of the air will suffice for calculating the moisture content of the air, and the same of course applies to other gases and vaporous components.

One of the difficulties in obtaining ideal conditions for the psychrometric measurement is, however, that heat may be conveyed to or detracted from the moistened surface of the wet thermosensor by the liquid used for moistening this thermosensor, so that its temperature will assume a value higher or lower, respectively, than that at which dynamic equilibrium exists between the heat convection from the gas to the moistened surface and the heat consumption for vaporization from that surface. To limit this source of error it is necessary in the case of the known psychrometers to keep the amount of liquid per time unit used for the moistening as small as possible, but still sufficient for keeping the wet thermosensor completely moistened. In the known psychrometric methods the total quantity of liquid supplied to the wet thermosensor is normally vaporized. Impurities in the supply liquid and dust, salt and oil drops precipitated from the gas flow will therefore be accumulated in the liquid film covering the wet thermosensor whereby the vapor pressure of the liquid will be reduced, and it becomes difficult to moisten the thermosensor efficiently, whereby measuring errors will occur. It is therefore necessary in the known methods to clean the wet thermosensor frequently.

The required rate of liquid supply to the wet thermosensor depends strongly on the degree of saturation of the gas in respect of the vaporous component in question. Therefore, in carrying out the known methods it is difficult to avoid a partial drying-up of the wet thermosensor at low degrees of saturation without at the same time invalidating the measurement at high degrees of saturation as a consequence of a too high rate of liquid supply.

The last-mentioned difficulties have been avoided in a psychrometric measuring apparatus disclosed in U.S. Pat. No. 3,157,049. In this apparatus the wet thermosensor is arranged at the bottom of an open flat dish, in which a thin liquid layer is present, the level of which is maintained constant by the supply of liquid through a level control device. Thus, in this apparatus an amount of liquid is at any time supplied to the wet thermosensor which is exactly the same as the amount removed by vaporization. However, it is not avoided that heat can be conveyed to or detracted from the wet thermosensor by the liquid supplied thereto, whereby measuring errors can occur as above described, particularly in the case of low degree of saturation of the gas in respect of the vaporous component, and it is not avoided either that impurities in the supply liquid and dust, salt, oil drops and the like precipitated from the gas flow will be accumulated in the layer of liquid covering the wet thermosensor so that a careful watch and frequent cleaning of the container will be required to obtain security against measuring errors resulting from pollution.

SUMMARY OF THE INVENTION

It is the object of the invention to provide a psychrometric method in which measuring errors resulting both from the transportation of heat with the liquid supply to the wet thermosensor and from pollution of the liquid is reduced to a minimum or practically completely eliminated.

According to the invention, liquid for moistening the "wet" thermosensor is caused to flow upwardly through a vertical tube, in the upper open end of which the "wet" thermosensor is arranged, in a flow of sufficient size for forming, on top of the tube, a body of liquid completely covering the thermosensor and the upper marginal edge of the tube, the body of liquid having a free surface swept by the gas flow, and for overflowing from the top of the tube down along the outer surface of the tube in the form of a continuous liquid film, the dimensions and material of the tube being so selected that the liquid flow, during its passage upwardly through the tube, by heat exchange with the liquid film on the outer surface of the tube, is brought to the same or practically the same temperature as that prevailing in the body of liquid on top of the tube.

Hereby the advantage is obtained that the vaporization of liquid and the heat convection determining the temperature of the wet thermosensor takes place from and to the surface area of a small volume of liquid immediately surrounding the thermosensor, to which area the liquid is supplied at the temperature already prevailing in the liquid volume and from which the liquid is again removed at the same temperature by overflowing the top edge of the tube. The liquid flow will therefore neither convey heat to nor detract heat from the volume of liquid immediately surrounding the thermosensor, and the temperature measured by the wet thermosensor will therefore within wide limits be independent of the rate of the liquid flow. The amount of liquid per time unit can therefore be made much larger than necessary for avoiding drying-up. By utilizing this circumstance the advantage is obtained that impurities in the supply liquid and impurities precipitated from the air on the moistened thermosensor will not be accumulated thereon, but will constantly be removed with the surplus flow of liquid flowing down along the outer surface of the tube.

Since both the vaporization of liquid from the surface area determining the temperature of the thermosensor and the convective supply of heat from the air to this area depend on the speed of the air in the same manner, the temperature of the thermosensor will also be independent of the speed of the air provided that this is made sufficiently high.

The invention also relates to an apparatus for use in carrying out the method described. The apparatus comprises in known manner a dry thermosensor and a wet thermosensor, and the features distinguishing of the invention are that it comprises a vertical tube with an opening at its upper end, a thermosensor constituting the wet thermosensor being arranged in or immediately adjacent the opening of the tube, and means for supplying a liquid to the lower end of the tube in a flow of sufficient size for forming, on top of the tube, a body of liquid completely covering the thermosensor and the upper marginal edge of the tube, the body of liquid having a free surface swept by the gas flow, and for overflowing from the top of the tube down along the outer surface of the tube in the form of a continuous liquid film, the dimensions and material of the tube being so selected that the liquid flow, during its passage upwardly through the tube, by heat exchange with the liquid film on the outer surface of the tube, is brought to the same or practically the same temperature as that prevailing in the body of liquid on top of the tube.

By mounting the supply conductors and supporting means of the wet thermosensor in the liquid-filled tube the advantage is obtained that the temperature gradient in the zone immediately adjacent the thermosensor can be made as low as desired by suitable selection of the length of the tube. Hereby the source of error inherent in the heat exchange of the thermosensor with the surroundings by heat conduction is eliminated.

BRIEF DESCRIPTION OF THE FIGURE

The accompanying Figure shows a schematic side view of one embodiment of an apparatus according to the invention.

DETAILED DESCRIPTION OF THE PREFERRED EMBODIMENT

The apparatus and the method will in the following be described as applied to the measurement of the moisture content of air, but it may in exactly the same manner be used for measuring the concentration of other vaporous components in other gases.

In the drawing 1 is a vertical tube, which is mounted on the bottom of a dish 2. The lower end of the tube, which is located below the dish, is closed by means of a plug 3, and immediately above the latter a water supply conduit 4 is connected to the tube. The upper end 5 of the tube 1, which is located high above the dish, is open. A supporting rod 6 is passed through the plug 3 and extends all the way up through the tube 1 and carries at its upper end a thermosensor 7, which is located in the mouth 5 of the tube 1. The supply conductors for the thermosensor 7 extend up through the supporting rod 6 and may, e.g., by moulded into the rod. For centering the supporting rod 6 and thereby the thermosensor in the tube 1, supporting members, not shown, may be provided between the supporting rod and the wall of the tube. At the bottom of the dish 2 a draining opening 8 is provided, which is connected to a drain pipe 9.

When water is supplied through the conduit 4, it flows up through the tube and forms at the top thereof a small body of liquid 10, from which the water overflows down along the outer surface of the tube 1 in the form of a continuous water film 11, which flows down into the dish 2 and is discharged through the drain 9. At some distance above the upper end of the tube 1 a thermosensor 12 is arranged. The flow of air, the moisture content of which is to be measured, flows past the tube 1 and the thermosensor 12 in a horizontal direction as indicated by an arrow 13, or in downward direction.

When the surface of the body of liquid is swept by the flow of air an evaporization takes place from the surface, whereby heat is removed from the surface. Hereby the temperature of the surface drops below the temperature of the air and heat is consequently transferred by convection from the air to the surface. When the temperature has dropped to a value such that the heat consumed for evaporation and the heat transferred by convection per time unit are equal, a state of equillibrium is established, where the temperature no more changes. The equilibrium temperature thus achieved depends on the moisture content of the air. When the measurement is performed continuously, this temperature of equilibrium will vary when the moisture content of the air varies.

The water film 11, too, is swept by the air so that a vaporization and at the same time a heat exchange with the air flow by convection take place. Through the wall of the tube heat exchange also takes place between the water film and the water flow up through the tube, and the temperature of the water film will therefore change down along the tube. If the tube is sufficiently long, the flow of water in the tube, when reaching the mouth of the tube, will be brought to the same temperature as that at which the water overflows the edge of the mouth 5. The total flow of water will therefore neither convey heat to the body of liquid 10 nor remove heat therefrom. The equilibrium temperature of the surface of the body of liquid and thereby of the body of liquid as a whole will therefore within wide limits be practically independent of the amount of water supplied per time unit and of the temperature at which the water is supplied to the lower end of the tube. This equilibrium temperature is the temperature measured by the thermosensor 7, which thus constitutes a wet thermosensor which has been liberated from influence by the amount of water supplied per time unit. It is therefore possible to use a flow of water much larger than the amount of water vaporized from the moistened surface. Hereby both drying-up of the moistened surface and the accumulation of impurities in the water film are avoided as previously mentioned.

By suitably selecting the length of the vertical tube 1, the vertical temperature gradient immediately below the upper mouth of the tube can be made arbitrarily small, whereby the heat conduction longitudinally through the tube as well as through supply conductors to and supporting means for the thermosensor can be made arbitrarily small.

With increasing speed of the air flow past the moistened temperature sensor the relative significance of the heat exchange between the sensor and the surroundings by radiation decreases, because the convective heat transmission increases with the air speed, while the heat radiation is independent of the air speed. Owing to the fact that a large flow of water is permissible, the air speed may also be made high without risk of partial drying-up of the moistened surface. By using a high air speed, a lower time constant of the two thermosensors 7 and 12 is also obtained.

The thermosensor 12, which constitutes the dry thermosensor for measuring the temperature of the air, must, in order to fulfill this function, be so arranged relatively to the wet thermosensor 7 that the air temperature measured is not disturbed by the exchange of heat and matter taking place at the surface of the body of water 10.

The parts of the apparatus shown in the drawing may be mounted in a housing, with which an air pump may be associated, or the parts may be mounted in a frame or directly in an air passage in which the moisture content of the air is to be measured.

I claim:

1. Method for the continuous psychometric measurement of the concentration of a vaporous component in a gas by causing the gas to flow past a "dry" thermosensor measuring the temperature of the gas flow, and a "wet" thermosensor, the surface of which is kept completely moistened with liquid of the same kind as the vaporous component, wherein liquid for moistening the "wet" thermosensor is caused to flow upwardly through a vertical tube, in the upper open end of which the "wet" thermosensor is arranged, in a flow of sufficient size for forming, on top of the tube, a body of liquid completely covering the thermosensor and the upper marginal edge of the tube, said body of liquid having a free surface swept by the gas flow, and for overflowing from the top of the tube down along the outer surface of the tube in the form of a continuous liquid film, the dimensions and material of the tube being so selected that the liquid flow, during its passage upwardly through the tube, by heat exchange with the liquid film on the outer surface of the tube, is brought to the same or practically the same temperature as that prevailing in the body of liquid on top of the tube.

2. Apparatus for use in the continuous psychometric measurement of the concentration of a vaporous component in a gas, comprising a "dry" thermosensor for measuring the temperature of a flow of the gas and a "wet" thermosensor likewise subjected to the flow of gas, but having its surface completely moistened with liquid of the same kind as the vaporous component, wherein said apparatus comprises a vertical tube with an opening at its upper end, a thermosensor constituting the "wet" thermosensor being arranged in or immediately adjacent the opening of the tube, and means for supplying a liquid to the lower end of the tube in a flow of sufficient size for forming, on top of the tube, a body of liquid completely covering the thermosensor and the upper marginal edge of the tube, said body of liquid having a free surface swept by the gas flow, and for overflowing from the top of the tube down along the outer surface of the tube in the form of a continuous liquid film, the dimensions and material of the tube being so selected that the liquid flow, during its passage upwardly through the tube, by heat exchange with the liquid film on the outer surface of the tube, is brought to the same or practically the same temperature as that prevailing in the body of liquid on top of the tube.

3. Apparatus as in claim 2, including supply conductors to and supporting means for the wet thermosensor, said supply conductors and supporting means being arranged in the tube.

* * * * *